United States Patent [19]

Kollar

[11] Patent Number: 5,463,119
[45] Date of Patent: Oct. 31, 1995

[54] RECYCLING PROCESS FOR THE PRODUCTION OF ADIPIC ACID AND OTHER ALIPHATIC DIBASIC ACIDS

[76] Inventor: John Kollar, Pittsburgh, Pa.

[73] Assignee: Redox Technologies Inc., Wyckoff, N.J.

[21] Appl. No.: 203,453

[22] Filed: Feb. 28, 1994

Related U.S. Application Data

[63] Continuation of Ser. No. 53,788, Apr. 26, 1993, abandoned, which is a continuation-in-part of Ser. No. 951,636, Sep. 25, 1992, abandoned.

[51] Int. Cl.$^6$ ................................................. C07C 51/31
[52] U.S. Cl. ........................................................ 562/543
[58] Field of Search ............................................. 562/543

[56] References Cited

U.S. PATENT DOCUMENTS

| | | |
|---|---|---|
| 2,223,493 | 12/1940 | Loder . |
| 2,589,648 | 3/1952 | Wadsworth ........................ 260/533 |
| 3,231,608 | 1/1966 | Kollar . |
| 3,390,174 | 6/1968 | Schulz et al. ........................ 260/533 |
| 3,657,334 | 4/1972 | Kulrestha et al. .................. 260/531 R |
| 4,032,569 | 6/1977 | Onopchenko et al. ............. 260/533 C |
| 4,158,739 | 6/1979 | Schulz et al. ....................... 562/543 |
| 4,263,453 | 4/1981 | Schulz et al. ....................... 562/543 |
| 5,221,800 | 6/1993 | Park et al. .......................... 562/543 |

FOREIGN PATENT DOCUMENTS

1304855  1/1973  United Kingdom .

OTHER PUBLICATIONS

G. N. Kulsrestha et al in J. Chem. Tech. Biotechnol., 50, 57–65 (1991).
K. Tanaka in Chemtech, 555–559 (1974).
Hydrocarbon Processing, 53, 114–120 (1974).

*Primary Examiner*—José G. Dees
*Assistant Examiner*—Joseph M. Conrad, III

[57] ABSTRACT

The invention relates to a process for the oxidative preparation of $C_5$–$C_8$ aliphatic dibasic acids by (1) reacting
  (a) at least one saturated cycloaliphatic hydrocarbon having from 5 to 8 ring carbon atoms in the liquid phase and
  (b) an excess of an oxygen-containing gas in the presence of
  (c) a solvent comprising an organic acid containing only primary and/or secondary hydrogen atoms and
  (d) at least about 0.002 mole per 1000 grams of reaction mixture of a polyvalent heavy metal catalyst;

(2) removing the aliphatic dibasic acid; and (3) recycling intermediates, post-oxidation components, and derivatives thereof remaining after removal of the aliphatic dibasic acid into the oxidation reaction.

22 Claims, No Drawings

RECYCLING PROCESS FOR THE PRODUCTION OF ADIPIC ACID AND OTHER ALIPHATIC DIBASIC ACIDS

This application is a continuation of application Ser. No. 08/053,788 filed Apr. 26, 1993, now abandoned which is a continuation-in-part of Ser. No. 07/951,636 filed Sep. 25, 1992 now abandoned.

BACKGROUND OF THE INVENTION

The present invention relates to a process for the preparation of $C_5$–$C_8$ aliphatic dibasic acids by oxidation of the corresponding saturated cycloaliphatic hydrocarbons in the presence of an organic acid solvent and a metal catalyst and subsequent recycling of the partly oxidized intermediates into the oxidation mixture for further oxidation.

Adipic acid is a major article of commerce and its preparation has, therefore, attracted much attention. Consequently, many processes for the production of adipic acid have been proposed. For example, one process involves nitric acid oxidation of cyclohexanol, cyclohexanone, or mixtures thereof, which can in turn be obtained by air oxidation of cyclohexane or hydrogenation of phenol. Several of these known processes are practiced commercially, but all suffer from high costs associated with such multi-step operations and the use of nitric acid, as well as from significant environmental pollution problems caused by the discharge of ozone-depleting nitrogen oxide by-products generated during nitric acid oxidation.

Processes that have been proposed for preparing dibasic acids without the use of nitric acid include air oxidation of saturated cyclic hydrocarbons and/or corresponding cyclic ketones and/or alcohols. For example, U.S. Pat. No. 3,390,174 and British Patent 1,304,855 disclose processes requiring mixtures of two or more of these components. However, many such air oxidation processes are multistep processes having poor selectivities and requiring difficult high-cost recovery processes.

Catalytic air oxidation processes are believed to involve free radical oxidation. Such oxidations are complex systems in which many types of reactions other than oxidation can occur. Free radicals will attack any C—H bonds, regardless of form, to an extent determined by bond strength and relative concentration of the specific C-H bond. As oxidation proceeds, various oxygenated compounds form, such as alcohols, aldehydes, ketones, and acids (including difunctional compounds having these functionalittes), as well as other low molecular weight carbon compounds. All of these compounds can further react via acid catalysis or thermal ionic mechanisms to form various condensation products, the most prevalent being esters. In general, the amount of condensation products will increase as the rate of oxidation relative to ester formation decreases. Process modifications that improve the ratio of oxidation to ester formation would be expected to yield a greater amount of easily recoverable diacid. In addition, modifications that lower the rate of esterification would be expected to improve the amount of easily recoverable diacid.

Until now, however, the seemingly attractive direct oxidation routes have not provided a viable commercial process, possibly because of the complexity of the reaction residues ("bottoms") containing inter alia many different simple esters derived from the various intermediates, oxidation products, and post-oxidation products. Such complexity is not unique to saturated cyclic alkane oxidations. Complex reactions exist even for oxidations of aromatic compounds such as xylenes. The primary distinction is that bottoms from methyl-substituted aromatic oxidation (i.e., intermediates, derivatives, and the like) can be subjected to very stringent oxidation conditions that allow further oxidation to oxidation-stable aromatic acids. For example, the aromatic acid products are extremely stable to further oxidation and can be subjected to extreme conditions under which a substantial amount of even seemingly inert acetic acid would be oxidized to $CO_2$ and water. Consequently, these aromatic acid products can be produced substantially free of oxidation bottoms, intermediates, derivatives, and the like at very high conversions of 95% or higher.

Aliphatic diacids such as adipic acid, on the other hand, are subject to further oxidation because the C—H bonds of the methylene groups in such acids can more readily undergo free radical attack and oxidation. If subjected to forcing oxidation conditions at higher conversion, the various bottoms, intermediates, and derivatives will oxidize (as do similar aromatic compounds). However, because of the relative instability to oxidation of the aliphatic acids (such as adipic, glutaric, and succinic acids, and even acetic acid under stringent conditions), these acid products and their derivatives will progressively and increasingly degrade to $CO_2$ and water, thereby providing lower selectivity.

Single-step direct air oxidation processes for the production of dibasic acids have been proposed. However, previously known one-step processes have been attended by poor selectivities, low production rates, multi-step operation, burdensome and costly separation steps, and low ultimate overall yields of dibasic acids from the saturated cyclic hydrocarbon. For example, U.S. Pat. No. 2,223,493 discloses a process for the direct oxidation of cyclohexane to form adipic acid at a reported production rate of 3.1 wt. % per hour in a concentration of 12.4 wt. % in the oxidation effluent with an overall selectivity of 46 to 49 mole %. This oxidation was carried out using a comparatively high concentration of cyclohexane (about 61 to 63 wt. %) in acetic acid solvent in the presence of air and various catalysts at temperatures of from 95° C. to 120° C. until a conversion level of about 23 to 24% was achieved.

U.S. Pat. No. 2,589,648 discloses a single-step oxidation process in which acetone is used instead of acetic acid as solvent.

U.S. Pat. No. 3,231,608 discloses another single-step direct oxidation process for the production of dibasic aliphatic acids. The reference teaches that certain critical ratios of solvent and catalyst to the saturated cyclic hydrocarbon can yield dibasic aliphatic acids under mild reaction conditions, usually at production rates of adipic acid of 3.5 to 4.0 wt. % per hour and at efficiencies generally around 73 to 76 wt. %. (It may be noted that, because adipic acid is the primary product of cyclohexane oxidation that has the highest possible molecular weight, the unit "wt. percent" will be higher than the usual selectivity-indicating unit "mole percent". In general, therefore, the reported efficiencies will be from about 2.8 to as much as 5 percentage points lower on a mole percent basis.) In particular, the reference teaches that molar ratios of solvent to saturated cyclic hydrocarbon in the range of 1.5:1 to 7:1 (or more) are suitable but that molar ratios below or above this range give unsatisfactory results.

Additional references describe attempts to improve upon the process of U.S. Pat. No. 3,231,608. A general objective of these references was attainment of higher conversions of cyclohexane, which was usually achieved by lowering the starting concentration of cyclohexane, by using protracted reaction times, or by making other such changes, with the result being very low reaction rates, reduced selectivities, and expensive recovery and downstream processing. For example, U.S. Pat. Nos. 4,032,569 and 4,263,453 require a greater relative amount of cobalt(III) catalyst (and U.S. Pat. No. 4,263,453 also requires small amounts of water) but still specify essentially the same molar ratios of solvent to cycloalkane as described in U.S. Pat. No. 3,231,608. G. N. Kulsrestha et al in *J. Chem. Tech. Biotechnol.*, 50, 57–65 (1991), similarly discloses an oxidation process that uses a relatively large excess of acetic acid and a relatively large amount of cobalt(III) catalyst. U.S. Pat. No. 4,158,739 discloses a similar preparation of glutaric acid from cyclopentane in which the molar ratio of solvent to cyclopentane must be at least 1.5:1 and the amount of catalyst is relatively higher than for the process disclosed in U.S. Pat. No. 3,231,608. In general, the use of excess acetic acid solvent at the higher molar ratios disclosed in the prior art appears to reduce the rate of adipic acid product.

Further details on a known single-stage oxidation process for the preparation of adipic acid from cyclohexane are discussed by K. Tanaka in *Chemtech*, 555–559 (1974), and *Hydrocarbon Processing*, 53, 114–120 (1974).

The complexities involved in the recovery of adipic acid are clearly evident from the above references. Although the formation of certain oxidation intermediates that are themselves oxidizable and recyclable (such as cyclohexanol and cyclohexanone) is known, difficulties associated with the compositional complexity of the "bottoms" (or residue) from the cycloalkane oxidation, whether related to controlling the formation of the bottoms or to handling their disposition, have not been resolved by the known methods.

For example, British Patent 1,304,855 discloses the direct oxidation of cyclohexanol, cyclohexanone, and cyclohexane, which is in a sense somewhat similar to oxidizing cyclohexane in the presence of recycled cyclohexanol and cyclohexanone. However, the references disclose a selectivity to adipic acid of only 54 mole % based on all oxidized cyclic six carbon compounds.

U.S. Pat. No. 3,390,174 discloses the oxidation of saturated $C_5$–$C_8$ cyclic hydrocarbons in the presence of the equilibrium concentrations of the corresponding cyclic alcohols and ketones. For example, for the oxidation of cyclohexane, the reference indicates that oxidation equilibrium levels are about 14 to 24% cyclohexanol and about 30 to 40% cyclohexanone, based on the amount of cyclohexane. However, the reported selectivities of cyclohexane to adipic acid are again only about 45 to 52 mole %.

Cyclohexanol and cyclohexanone are more readily oxidized to produce lower oxidation equilibrium levels than are cyclohexanol esters, which are among the primary constituents of the bottoms. In general, for example, an alcohol is oxidized four to five times faster on a relative molar rate basis than an ester of the same alcohol, resulting in a molar concentration of esters at oxidation equilibrium that is four to five times higher than the equilibrium level of the corresponding alcohol. Thus, when using methods that depend on the presence of cyclohexanol and cyclohexanone, the buildup of esters in the bottoms would be expected to adversely affect the efficiency of adipic acid production.

The inferior results described above can generally be attributable to the difficulty of attaining good molar selectivities by the direct oxidation of cyclohexane. Molar selectivities to adipic acid in the 80 mole % range have been achieved only when using air oxidizing oxygenated cyclic compounds such as cyclohexanone and/or cyclohexanol. For example, British Patent 1,237,479. However, these methods suffer from the disadvantages of multi-step operations, which include the generally costly production of the oxygenated cyclohexanol and/or cyclohexanone by oxidation of cyclohexane at typically very low conversions and at selectivities of about 80–92 mole %. Thus, when the complexity and multiplicity of operating steps are taken into consideration, the overall process selectivity to adipic acid is at best only about 70–79 mole %.

It has now been found possible, however, to prepare dibasic acids by the oxidation of saturated cycloalkanes by a process having very desirable commercial features. In particular, it has now been found that the ultimate obtainable selectivity and overall recovery of dibasic acids prepared by the oxidation of saturated cycloalkanes can be improved by minimizing the formation of bottoms, returning intermediates and derivatives (including the complex bottoms), optionally after partial further treatment, to the oxidation environment, and working up after oxidation. Indeed, the direct air oxidation of cyclohexane can be achieved at molar selectivities virtually identical to the best air oxidation of the facilely oxidized cyclohexanone and cyclohexanol. Moreover, the oxidation of cyclohexane, according to the process of this invention, is attended by a low production of CO and $CO_2$, which reflects the amount of degradation of the $C_6$ structure.

SUMMARY OF THE INVENTION

Accordingly, the present invention relates to a process for the oxidative preparation of $C_5$–$C_8$ aliphatic dibasic acids comprising (1) reacting
   (a) at least one saturated cycloaliphatic hydrocarbon having from 5 to 8 ring carbon atoms in the liquid phase and
   (b) an excess, relative to cycloaliphatic hydrocarbon (a), of oxygen gas or an oxygen-containing gas mixture
in the presence of
   (c) 0.15 to 15 moles (preferably 0.25 to 3.0 moles and more preferably 0.25 to ).5 moles) of a solvent per mole of cycloaliphatic hydrocarbon (a), wherein said solvent comprises an organic acid containing only primary and/or secondary hydrogen atoms and
   (d) at least about 0.002 mole (preferably 0.015 to about 0.3 mole) per 1000 grams of reaction mixture of a polyvalent heavy metal catalyst (preferably a cobalt salt of an organic acid);

(2) removing the aliphatic dibasic acid (preferably as a precipitate collected by filtration or centrifugation); and (3) recycling intermediates, post-oxidation components, and derivatives thereof remaining after removal of the aliphatic dibasic acid (optionally in the presence of residual solvent, optionally after hydrolysis and isolation of additional aliphatic dibasic acid, and optionally after addition of further quantities of saturated cycloaliphatic hydrocarbon (a)) into reaction step (1) for reaction with oxygen gas or an oxygen-containing gas mixture in the presence of solvent (c) and catalyst (d) and subsequent isolation of aliphatic dibasic acid and, optionally, further recycling.

DETAILED DESCRIPTION OF THE INVENTION

The process of this invention involves a single-stage oxidation that subjects a saturated cycloalkane and recycled bottoms to mild oxidation conditions, one of the important features being the intentional limitation of the extent of conversion of the cycloalkane. Thus, for example, when the feed cyclic alkane is cyclohexane, the primary product is adipic acid.

Suitable cyclic hydrocarbons for use in the process of the invention include saturated cyclic hydrocarbons having from 5 to 8 ring carbon atoms and containing only primary and secondary hydrogen atoms. Examples of suitable saturated cyclic hydrocarbons include cyclopentane, cyclohexane, cycloheptane, cyclooctane, or hydrocarbon analogs or homologs thereof that contain only primary and secondary hydrogen atoms. A particularly preferred cyclic hydrocarbon is cyclohexane, which is a readily available commercial product.

The cyclic hydrocarbon component may also contain any substantially inert diluent, such as another hydrocarbon containing only primary and secondary hydrogens. In general, however, such diluents are preferably removed, especially if present in larger amounts, because they necessarily occupy reactor space. A particularly beneficial inert diluent is benzene, the ultimate source of commercially produced cyclohexane. The presence of benzene can be economically advantageous for the production of adipic acid by enhancing the rate of oxidation and by allowing the use of lower grade cyclohexane from which benzene need not be removed.

In particular, when preparing adipic acid from cyclohexane according to the invention, the cyclohexane can contain substantial amounts of benzene without detrimental effect on the oxidation process. In fact, when benzene replaces a portion of solvent (c) (e.g., acetic acid), the rate of oxidation may even be improved. For example, the presence of up to about 60% by weight of benzene relative to cyclohexane can increase the oxidation rate.

In addition, cyclohexane is produced commercially by hydrogenation of benzene. The conditions for hydrogenation are generally harsh, so as to optimize conversion and to minimize the cost associated with the difficult separation of benzene from the cyclohexane product. Thus, for example, the use of cyclohexane containing 0.1 wt. % (or less) up to 5 or 10 wt. % of benzene can reduce raw material costs. Consequently, the more favorable oxidation kinetics and less demanding distillation requirements would permit substantially greater production of cyclohexane from an existing cyclohexane facility.

The oxidant used in the process of the invention can be essentially any gas containing free molecular oxygen and optional substantially inert gaseous diluents. Examples of suitable oxygen-containing gases are air and oxygen-enriched air (that is, air having an augmented oxygen content of, for example, 85 mole percent or more), as well as pure gaseous oxygen. A mixture of 50 wt. % oxygen and 50 wt. % nitrogen, for example, provides satisfactory results. Even oxygen-depleted air can be used but is less preferred. Any gases that are substantially inert under the reaction conditions are suitable gaseous diluents. Examples of such gaseous diluents include nitrogen, carbon dioxide, helium, neon and argon, as well as the normally gaseous paraffin hydrocarbons (such as methane, ethane, and propane). Mixtures of diluents can, of course, also be used. Regardless of the oxygen-containing gas used, the molar quantity of oxygen should be at least sufficient to provide complete oxidation of the cycloaliphatic hydrocarbon to the corresponding dibasic acid (that is, at least 2.5 moles of $O_2$ for each mole of cycloaliphatic hydrocarbon).

The partial pressure of oxygen over the reaction mixture should be at least 0.10 atmosphere absolute and can be as high as 100 atmosphere absolute, or even higher. The preferred partial pressure of oxygen over the reaction mixture should be from at least about 0.10 to about 0.30 atmospheres absolute. The total pressure should be at least sufficient to keep the reactants in the liquid phase. The total reaction pressure that is employed will depend to a large extent on the particular oxygen-containing gas which is used, the composition of the reacting mixture, and temperature, which together determine the vapor pressure of the liquid reacting mixture.

Suitable solvents for use as component (c) of the invention can be essentially any weak organic acids that contain only primary and/or secondary hydrogen atoms (that is, organic acids in which hydrogen atoms other than those of COOH groups are attached only to primary and/or secondary carbon atoms). Preferred solvents include lower aliphatic monocarboxylic acids having 2 to about 6 carbon atoms, more preferably acetic acid. Mixed solvents (including mixtures of solvents with inert diluents such as benzene) can, of course also be used. The amount of solvent used is selected so that from about 0.15 to about 15 moles (preferably about 0.25 to about 3 moles and more preferably 0.25 to 1.5 moles) of solvent are present in the oxidation zone for each mole of the cycloaliphatic hydrocarbon. When oxidizing cyclohexane in acetic acid solvent, for example, this molar ratio range corresponds to a concentration of about 8.5 wt. % up to about 91 wt. % cyclohexane and about 91.5 wt. % down to about 9 wt. % acetic acid, with the preferred relative quantities corresponding approximately to 30–85 wt. % cyclohexane and 15–70 wt. % acetic acid and more preferably 50–85 wt. % cyclohexane and 15–50 wt. % acetic acid. For cycloheptane or cyclooctane, which have higher molecular weights than cyclohexane, the corresponding weight percentages of the cycloalkane will, of course, be greater, whereas for cyclopentane, the corresponding weight percentage will be less.

Suitable oxidation catalysts are conventional in nature and include polyvalent heavy metal catalysts, especially those having atomic numbers from 23 to 29, as well as cerium. Particularly preferred catalysts are those containing cobalt, manganese, vanadium, and cerium and combinations thereof. These heavy metal catalysts are supplied to the oxidation zones in the form of compounds that are soluble or will become at least partially solubilized under the conditions of the oxidation reaction. Suitable such compounds include the oxides, hydroxides, and, preferably, the inorganic and organic salts of the metals. It is particularly preferred to use the catalyst metals as their acetates, naphthenates, and toluates, as well as various fatty acid salts, such as stearates, oleates, and the like.

The preferred catalysts include essentially any cobalt salt of an organic acid. Examples of suitable such catalysts include cobalt acetate, cobalt propionate, and cobalt naphthenate. Materials which form such cobalt salts in situ can also be employed. For example, cobalt oxide and acetic acid are suitable because they will form cobalt acetate in situ. It is particularly preferred for the cobalt salt to correspond to the salt of the acid which is used as the reaction solvent. Because acetic acid is the preferred solvent, cobalt(II) acetate is the most preferred catalyst.

The concentration of catalyst required within the oxidation zone is somewhat dependent on the desired rate of oxidation. Accordingly, preferred amounts of catalyst vary from about 0.005 to about 0.6 mole per 1000 grams of reaction mixture (more preferably between about 0.015 and about 0.3 mole per 1000 grams and most preferably between about 0.03 and about 0.20 mole per 1000 grams). Of course, substantially greater amounts of catalyst (for example, up to 1 mole per 1000 grams or even more) can be employed, but the use of such large quantities provides little advantage and, in fact, the use of such large quantities can cause problems in recovery of catalyst for recycle and re-use.

It is not necessary to use extraneous promoters, initiators, and the like in the process of the invention. Such extraneous materials can give slightly improved rates and/or conversion and/or selectivities, but their use generally increases cost and may result in the formation of by-product. Thus, such additives are normally not used. However, if special circumstances warrant their use, it is possible to use extraneous promoters such as, for example, acetaldehyde, methyl ethyl ketone, cyclohexanol, cyclohexanone, and the like.

Contrary to the expectations of the prior art, the oxidation of high concentrations of cycloalkanes at low conversion levels provides advantageous chemical and economic results. As used herein, the term "conversion" refers to the ratio (usually expressed as a percentage) of the quantity of cycloalkane that reacts in any manner to the quantity of cycloalkane in the feedstock. Stated another way with reference to oxidation products and by-products, the term "conversion" refers to the total moles of all dibasic acids produced (for example, the sum of adipic acid, glutaric acid, and succinic acid prepared when oxidizing cyclohexane) and the various by-products to the moles of the cycloalkane in the feedstock. For example, when oxidizing cyclohexane, the use of high cyclohexane concentrations at restricted conversion levels, in conjunction with mild reaction conditions and with catalysts such as cobalt(II) or cobalt(III) ion that generate free radicals in an organic acid/or mixed solvent, gives a rapid rate of adipic acid production with minimal structural loss of $C_6$ compounds (that is, with lower conversion to $C_5$, $C_4$, or lower of carbon-containing by-products).

The reaction conditions used according to the invention are particularly suited to the preferred separation and recycling method of the invention. In particular, carrying out the oxidation process under such conditions permits a surprisingly facile recovery of adipic acid because of the strong tendency of the oxidation effluent upon cooling to separate cleanly into phases. As a result, the non-polar upper phase can be directly recycled for oxidation without costly processing (although it is, of course, possible to concentrate or otherwise process the non-polar phase before recycling for oxidation). The polar lower phase can be extremely rich in adipic acid that can be recovered in high yield by filtration or centrifugation, with the filtrate or supernatant, respectively, being to a large degree directly returned to oxidation without costly reprocessing. (It is, of course, also possible to remove the adipic acid product before separating the liquid phases.) The bottoms contained in the small portion of filtrate that is further processed for recovery of succinic and glutaric acid can be subjected to hydrolysis (preferably thermal hydrolysis) to achieve further removal of dibasic acid and provide a recycle stream for oxidation that is richer in the more easily oxidizable alcohols.

The reaction conversion will increase with reaction time to yield a higher concentration of dibasic acids. However, it is preferable to limit the extent of conversion. For example, when oxidizing cyclohexane, the selectivity to adipic acid diminishes as the conversion of cyclohexane is increased. The dibasic acid products are subject to further oxidation and thus a loss of selectivity. Therefore, it is preferable for the average concentration of the dibasic acids to be kept at the lowest practical level consistent with recovery costs. Furthermore, since free radical oxidation attacks all oxidizable species in proportion to both reactivity and concentration, the presence of high concentrations of cycloalkane redirects the oxidation away from dibasic acids and their derivatives toward cycloalkane, thereby minimizing post-oxidative attack on the desired dibasic acid. Low concentrations of dibasic acid and high concentrations of cycloalkane in the oxidation zone (or, expressed alternately, low conversion) will maximize selectivity. The use of low conversion processes can sometimes have adverse economic consequences, but such adverse economic effects do not arise when using the high cycloalkane system of this invention because the desired dibasic acid product is facilely and economically precipitated and removed from the system as a solid. It is possible to improve upon all such oxidations of saturated cyclic alkanes by recycling bottoms according to this invention, but the appropriate selection of certain reaction parameters provides optimum chemical and economic results. When oxidizing cyclohexane, for example, it is preferable to limit the conversion per pass of cyclohexane to no more than about 75%. Although it is possible to achieve higher conversions of cyclohexane, adipic acid selectivities typically deteriorate. In general, optimal production of adipic acid is achieved when conversions are kept at about 7 to about 30% (preferably 10% to 30% and more preferably 15 to 25%) per pass.

When carrying out oxidations according to the invention, the reaction temperatures for the oxidation can vary from about 60° to about 175° C., with preferred temperatures being from 90° to 125° C. Temperatures below about 75° C. tend to result in undesirably low production rates of dibasic acids, whereas temperatures above about 150° C. tend to cause an increase in decarboxylation reactions (with concomitant release of $CO_2$). Accordingly, temperatures in the oxidation zone are preferably from 75° to 150° C. and most preferably from 90° to 125° C.

In contrast to these relatively precise temperature requirements, total pressure for the oxidation is generally not critical so long as it is sufficient to maintain a liquid phase. However, economic considerations associated with design and construction of the oxidation equipment normally dictate the use of pressures of from about 1 to about 100 atmospheres absolute (preferably from 1 to 70 atmospheres absolute and more preferably from 5 to 40 atmospheres absolute). On the other hand, the partial pressure of oxygen (measured in the vent gases from the oxidation zone) should be at least about 0.10 atmospheres absolute and preferably at least 0.3 atmospheres absolute. Maximum oxygen partial pressure is dictated almost entirely by flammability considerations.

The oxidation mixture is preferably well agitated to insure better contact of the reactants. Agitation can be provided by mechanical stirring devices optionally aided by the ebullition caused by the introduction of the oxygen-containing gas into the liquid reaction mixture.

The reaction time for the oxidation can vary from about ten minutes to about six hours (or even more), with preferred reaction times being about 0.25 to two hours.

A key feature of the present invention is the unexpectedly advantageous ability to recycle the intermediates and derivatives back into the oxidation reaction, despite the multitude of bottoms components. The process complexities connected with the presence of bottoms are related to such factors as the rate of bottoms formation during oxidation and post-oxidation, the equilibrium rate under the specific oxidation conditions, and the existence of many hundreds of compounds. The difficulties of dealing with the bottoms can be further complicated by a low rate of dibasic acid formation and by catalyst considerations. These difficulties are controlled by using oxidation conditions that promote more rapid formation of dibasic acid but are milder with respect to bottoms formation; by maximizing the amount of direct recycle back to oxidation in order to minimize post-oxidation exposure of the reaction effluent to higher temperatures, concentrations, and reaction times; and, optionally, by hydrolyzing the bottoms that are further processed in order to recover dibasic acid and recycle to oxidation a new stream that is higher in the more easily oxidized and lower equilibrium level alcohol components.

The hundreds of oxygenated components that constitute the bottoms can be grouped into two main broad classes of compounds. The first group of compounds are those that can be further oxidized to form desired products (or derivatives thereof) and can thus be considered intermediates. The second group of compounds, which includes the dibasic acid products and their derivatives, are, however, subject to post-oxidative attack that leads to loss of the desired product. For example, in the oxidation of cyclohexane, the bottoms may contain a myriad of components that serve as intermediates because they can be further transformed to adipic acid. Some components of the bottoms can be considered both intermediates and products. Another, generally less significant group of bottoms are post-oxidation components and derivatives that are formed by oxidation of the dibasic acids. This group of post-oxidation components can be transformed to less desirable (but still valuable) glutaric and succinic acids. In general, it is highly desirable to recycle intermediate components and even post-oxidation components but undesirable to recycle derivatized product.

Under low conversion conditions, the concentrations of oxidation intermediates are high relative to the total of all oxygenated materials and the concentrations of undesirable post-oxidation products are low. Under high conversion conditions, however, oxidation gives lower levels of oxidation intermediates and higher levels of undesired post-oxidation products and shorter carbon chain dibasic acid products (that is, lower dibasic acid selectivity). Although total dibasic acid selectivity can remain high at higher conversions, the selectivity to the desired longest chain dibasic acid (for example, adipic acid from cyclohexane) will deteriorate. As conversions and oxidation conditions are made more stringent, both total and specific dibasic acid selectivities will deteriorate.

Esters are typically the major component of the bottoms. The multitude of esters includes virtually all possible alcohol and acid functions (including difunctional and trifunctional compounds) derived from cyclohexanols, cyclic diols, cyclic hydroxy ketones, hydroxy acids, hydroxy diacids, acetic acid, and various diacids, as well as other linear multifunctional compounds. In general, the esters of greatest prominence will be those in which the alcohol and acid moieties are present in the reaction environment in the greatest concentrations, whereas the esters of least prominence will be those in which the alcohol and acid moieties are present in the reaction environments in lowest concentrations.

The amount of esters in the bottoms is a function not only of factors directly related to the oxidation procedure but also of factors related to the workup procedure. For example, when time, temperature, and concentration effects are greater after the oxidation than during oxidation, a greater amount of ester can be formed during workup.

The various esters of the bottoms, because of their differing component parts, will have different effects on the overall oxidation process, some positive and some negative. Those esters having component parts that can be oxidized to form the desired products can be considered intermediates, whereas, other esters, such as those derived from the desired final dibasic acid products, are subject to post-oxidative attack that can lead to loss of the desired product.

The removal of the aliphatic dibasic acid from the reaction mixture in a manner consistent with recycling can be carried out by a variety of separation and isolation methods known in the art. However, in a preferred embodiment of the invention, the dibasic acid is removed by (i) cooling the reaction mixture to induce precipitation of the aliphatic dibasic acid and separation of the liquid portion of the reaction mixture into a polar liquid phase and a non-polar liquid phase and (ii) separating the resultant precipitated aliphatic dibasic acid, polar liquid phase, and non-polar liquid phase from one another (preferably by phase separation followed by filtration or centrifugation or by filtration or centrifugation followed by phase separation). Recycling is then carried out by (i) transferring the non-polar liquid phase (which may contain residual solvent, as well as certain other constituents having a degree of solubility or miscibility in the non-polar phase), optionally, after addition of further quantities of saturated cycloaliphatic hydrocarbon (a), into reaction step (1) for further oxidation and isolation of aliphatic dibasic acid and, optionally, further recycling and (ii) transferring at least a portion of the polar liquid phase, optionally after hydrolysis and isolation of additional aliphatic dibasic acid and, optionally, after addition of further quantities of saturated cycloaliphatic hydrocarbon (a), into reaction step (1) for further oxidation and isolation of aliphatic dibasic acid and, optionally, further recycling. With respect to recycling the polar phase, it is in general suitable to transfer about 10 to about 98%, by weight (preferably 50 to 95% by weight and more preferably 60 to 90% by weight) of the polar phase, optionally, after the intermediate treatments mentioned above, into reaction step (1).

In a particularly preferred embodiment, the portion of the polar lower phase mother liquor that is not recycled directly back to oxidation (that is, the portion from which glutaric and succinic acids must be removed) is subjected to hydrolysis and recovery of free diacid so that the recycled stream has a higher relative amount of the more easily oxidizable alcohol function and a lower relative amount of the diacid. This hydrolysis step can provide effective control of bottoms at equilibrium during oxidation and facilitate adipic acid purification.

The water produced during the oxidation reaction, as well as any water added during the optional hydrolysis step, can be removed at any of several points in the overall process of the invention. For example, water can be removed by methods known in the art from the reaction mixture during the reaction or from the polar phase (preferably by distillation) before the polar phase is recycled.

The recycling steps of the invention may, of course, be carried out batchwise (as illustrated in the examples) or continuously using methods known in the art. Whatever the specific recycling methods employed, however, the molar ratio of solvent (c) to cycloalkane (a) should be maintained within the specified range.

The benefits that can be gained by controlling bottoms formation and recycling at an operable concentration below equilibrium, according to this invention, can vary somewhat. While all saturated cycloalkane oxidations can benefit from the practice of this invention, the invention is best exemplified by selection of certain operating conditions. For example, the benefits of the invention can be very substantial at low conversions but are of decreasing significance at very high conversions. Furthermore, these benefits are greatest when using high (rather than low) concentrations of cycloalkanes, when using oxidation conditions that are conducive to a rapid (rather than slow) rate of dibasic acid formation, when using milder oxidation conditions that are less conducive to bottoms formation, and when using milder and shorter post-oxidation conditions that are less conducive to bottoms formation. Proper selection of process conditions permit high recovery of the desired dibasic acid and maximum recycle to oxidation with only minimal ester formation during workup. For example, when using the preferred phase separation method, it is possible to maximize direct recycle of mother liquor. When oxidizing cyclohexane, total recycling to achieve ester equilibrium would require a relatively high total ester concentration of about 40 to about 50 wt. %, based on cyclohexane. However, this high level of polar oxygenated "bottoms impurities" makes the first crystallization of adipic acid more difficult and exposes a greater percentage of adipic acid derivatives to post oxidative attack to shorter carbon chain degradation products. In practice, the amount of bottoms in the oxidation of cyclohexane can be kept to a manageable steady state level of about 4–8%, based on cyclohexane, at conversion levels of 18–25%. This level of bottoms during oxidation, as compared to the natural oxidation equilibrium of as much as 50 wt. %, reduces the amount of post-oxidative attack on adipic acid esters and other dibasic acid esters.

Appropriate control of bottoms buildup and of recycling, based on various theoretical and experimental consideration, can be used to effect a higher overall selectivity and more complete and facile recovery of diacid products. Factors that can be adjusted to enhance selectivity and recovery of dibasic acid products include using lower conversion of higher concentration cycloalkane oxidates to give higher oxidation rates but lower rates of bottoms formation, as opposed to using higher conversion levels (especially above about 65%) and lower concentration cycloalkane oxidates at lower oxidation rates and higher rates of bottoms formation, which can lead to a deterioration in molar selectivity to dibasic acids; minimizing the extent of bottoms recycling to the oxidation step to attain a substantial equilibrium oxidation level that can be as high as 50 to 60% based on cyclohexane but can be held to about 4–8%; minimizing exposure of the oxidation effluents to temperature, time, and concentration effects, which can affect the amount of equilibrated bottoms (for example, by minimizing the use of downstream recovery processes that require higher temperatures, longer reacting times, and higher concentrations that lead to increased formation of bottoms); and using an optional hydrolysis step (preferably thermal hydrolysis) for a portion of the bottoms and subsequent removal and recovery of additional amounts of the desired dibasic acid and other dibasic acid products, such as glutaric and succinic acids, to control the amount of equilibrating bottoms in the oxidation.

The following examples further illustrate details for the advantageous process of the present invention. The examples emphasize the rate of adipic acid production and attainable selectivities, two critically important factors affecting capital costs and raw material costs. However, the invention, which is set forth in the foregoing disclosure, is not to be limited either in spirit or scope by these examples. Those skilled in the art will readily understand that known variations of the conditions of the following procedures can be used. Unless otherwise noted, all temperatures are given as degrees Celsius.

EXAMPLES

Throughout the examples the following terms have the meanings indicated:

Conversion—The ratio (expressed as a percentage) of the total moles of dibasic acids (that is, the sum of adipic acid, glutaric acid, and succinic acid) and ultimate losses to the moles of cyclohexane in the feedstock.

Reaction Rate—The weight percent (based on the total liquid-phase reaction medium) of adipic acid produced per hour (based on an extrapolation of the actual amount produced in the time described in each example).

Selectivity to Adipic Acid—The ratio (expressed as a percentage) of the moles of adipic acid formed to the number of moles of cyclohexane reacted and which cannot be recovered or recycled. This term is indicative of ultimate yield when non-product can be recovered and recycled.

Selectivity to Dibasic Acids—The ratio (expressed as a percentage) of the moles of all dibasic acid formed to the number of moles of cyclohexane reacted and which cannot be recovered or recycled. This term is indicative of ultimate yield.

The following gas-liquid chromatography (GLC) method was used for analytical determinations. The GLC analyses were carried out using columns having a diameter of 0.125 inch (ca. 3.2 mm) and varying lengths were packed with PEG 20M (that is, polyethylene glycol having a molecular weight of about 20,000) as the liquid substrate and an 80–100 mesh CHROMOSORB W support (available from Supelco Inc.; CHROMOSORB is a trademark of Johns-Manville Corporation) and fitted with a thermal conductivity detector. Samples were prepared for GLC analysis by converting the carboxylic acids to methyl esters. The methyl esters were prepared by mixing the sample with a fixed amount of excess methanol and about 5–10 wt. % of predried AMBERLYST 15 sulfonic acid resin (available from Rohm and Haas Company) and then heating over a steam bath for about one hour. Analytical standards for adipic acid, glutaric acid, and succinic acid, acetic acid (as well as other components for which quantization was desired) were prepared by the same technique using mixtures of known quantities of the pure compounds in ratios approximating those of the test samples. For example, for oxidations using 40% acetic acid medium, the standard was prepared using a mixture of acetic acid, water, adipic acid, glutaric acid, and succinic acid in a weight ratio of 5:1.25:1:0.1:0.05 and six parts of methanol for each part of the mixture. When analyzing the isolated dibasic acids for impurities (for example, the amounts of glutaric and succinic acids in adipic acid isolates) or when analyzing concentrated bottoms, the samples were prepared using 12 parts of methanol for each part sample. The standard for concentrated bottoms (which contains little if any cyclohexane, water, and acetic acid) can be prepared, for example, using a mixture of adipic acid, glutaric acid, and succinic acid in a weight ratio of 1:1:0.5 and 12 parts of methanol for each part of the mixture. Although the diesters are in equilibrium with smaller quantities of the free acids and monoesters under these conditions, this method provided accurate and reproducible results.

Oxidations are characterized by a typical "S curve" in graphs having oxidation rate plotted along the ordinate (i.e., the y axis) and time plotted along the abscissa (i.e., the x axis). The lower portion of the S curve is a combination of chemical and physical characteristics, being both a combination of a chemical induction period and heatup to reaction temperature. The sloping portion of the S curve is usually nearly constant for the major portion of the oxidation and serves as a good indicator of the rate of oxidation. The slope of the curve bends downward to become the top of the S curve only with the occurrence of a substantial reduction in the reactants and/or other oxidation limiting factors (such as phase separation), with an attendant drop in oxidation rate.

For measurement purposes, the starting time in the oxidations described in the examples is taken as the intercept of the slope of the S curve with the x-time axis. Furthermore, it is preferred to quench the oxidation before the top of the S curve is reached. In the zone where phase separation is beginning to occur, a disproportionate amount of oxidation of the catalyst-rich polar phase is believed to occur. This phase is rich in adipic acid and low in cyclohexane, conditions conducive to post-oxidation of adipic acid and deterioration in selectivity. Furthermore, this phase of the oxidation is a controllable feature of the reaction through removal of some water of reaction.

Unless otherwise indicated, the following procedure was employed for the experimental runs in the examples. A reaction mixture was formed by dissolving the catalyst in the solvent, adding the charge stock (which was cyclohexane in all of the examples), and an Initiator to a 500-ml 316 stainless steel reactor equipped with a rotating magnetic agitator. The reactor was then sealed and pressurized to 14 atmospheres absolute with a mixture of 50% oxygen gas and 50% nitrogen gas. The reaction mixtures were heated to the reaction temperature, and the progress of oxidation was measured by the pressure drop due to oxygen consumption. When approximately 70–80% of the oxygen was consumed, the system was repressurized with oxygen to the starting pressure. At the desired conversion level, the reaction was quickly quenched by cooling by about 20°–30° C. and then worked up.

After the reaction effluent was cooled to induce crystallization, the resultant three-phase effluent was filtered to recover adipic acid. The crystalline adipic acid was washed with cold acetic acid-cyclohexane and dried. The two-phase mother liquor and washes were handled in a manner designed to simulate a continuous operation, with all of the non-polar upper phase and most of the polar lower phase being directly recycled and not subjected to conditions that would form additional bottoms (i.e., reaction residue). The simulation was achieved by removing the water of reaction, as well as additional adipic acid, using conditions under which minimal ester formation occurs, that is, by removing cyclohexane, water, and most of the acetic acid at temperatures below 60° C. (usually 50° C.) under vacuum. After cooling, additional adipic acid was recovered from the resultant concentrate and washed with cold cyclohexane-acetic acid. The mother liquor, which contained bottoms, unrecovered adipic acid, and glutaric and succinic acids, was intensely dark green, a color indicative of cobalt(III) ion, the active free-radical-generating form of the catalyst. The mother liquor was analyzed for bottoms content and then reconstituted with additional cyclohexane, acetic acid, and a small amount of catalyst. In particular, the cyclohexane content was brought to the initial concentration; the additional acetic acid equaled the original starting quantity less the amount of recycled bottoms and unrecovered dibasic acids; and the additional catalyst replaced the amount removed during sampling.

The reconstituted reaction mixture containing recycle bottoms was oxidized under the same conditions as used in the initial reaction but was usually stopped after about 80% oxygen uptake. After quenching the oxidation by cooling the reaction mixture by about 20°–30° C., the reaction mixture was manipulated in the same way as the first sequence described above for recovery of adipic acid and preparation for additional recycle.

This simulation procedure was repeated through multiple cycles to establish that oxidation could be beneficially carried out in the presence of increasing but controlled amounts of bottoms while still achieving excellent results of rate and selectivity. Minor reduction in rate was observed as the concentrations of bottoms and/or dibasic acids were allowed to accumulate. However, this rate reduction was not severe at the controlled levels that could be maintained.

A second experimental setup used a one-liter glass reactor equipped with a turbine stirrer. In this oxidation setup, a 500 g liquid charge (a volume of about 600 to 620 ml) at room temperature was used. Oxygen was used as the oxidant at a partial pressure of 5 to 15 psta, using a minimal flow of excess oxygen. The workup and reconstitution of each subsequent oxidation charge was identical to the smaller 75 g scale recycle runs described above.

EXAMPLE 1

To the 500-ml 316 stainless steel reactor was added 45 g (535 mmoles) of cyclohexane, 30 g (500 mmoles) of acetic acid solvent, and 0.951 g (3.82 mmole) of cobalt(II) acetate tetrahydrate, as well as 0.1 g of acetaldehyde as an initiator to avoid an induction period. The reactor was sealed and pressurized to a pressure of 14 atmospheres with a mixture of 50% $O_2$ and 50% $N_2$. The reaction was then carried out at 95° C. for 1.5 hours. The system was repressurized with oxygen two times when the system pressure indicated consumption of 70–80% of the oxygen. After the reaction was stopped by cooling, the reaction mixture was worked up as described above to recover adipic acid and to prepare the bottoms (which contained catalyst) for recycling. The accumulating bottoms and catalyst were recycled three times for a total of four runs with the following results. By a combination of actual recovery and analysis it was found that the average rate of adipic acid production for the four runs was 12.8 wt %/hr based on the amount of the reaction mixture. The average conversion of cyclohexane was 21.2%. The selectivity to adipic acid was 87.2 mole %, to glutaric acid was 6.7 mole %, and to succinic acid was 3.7 mole %. About 69% of the total adipic acid was recovered by direct filtration of the cooled oxidation effluent. Based on equivalent processing of recycling all of the upper phase and 75% of the lower phase, the amount of bottoms at oxidation equilibrium was 4.3 wt % based on cyclohexane. The adipic acid that could be recycled was about 24.1% of the adipic acid made or about 7.7 wt % based on cyclohexane.

Over the course of the four runs, the rate of adipic acid formation dropped by about 24%. The oxidation rate was adversely effected by the amount of recycle of adipic acid, bottoms, and other dibasic acids. The selectivity to adipic acid is adversely affected by the amount of recycled adipic acid and bottoms because of post-oxidation of components containing adipic acid in derivatized form. This observation illustrates the advantages of removing the maximum amount of adipic acid and minimizing bottoms. Rate-inhibiting dibasic acids have not been removed in this and the other illustrative examples because of the difficulties inherent in quantitatively manipulating small volumes when carrying out high vacuum distillations. However, it is possible to remove the succinic and glutaric acids with a 75% bottoms recycle by flash distillation.

Example 1, when compared with the previously known methods, provides a much higher oxidation rate, significantly higher adipic acid selectivity, and greater ease of adipic acid recovery.

EXAMPLE 2

To the 500-ml 316 stainless steel reactor was added 22.5 g (267 mmoles) of cyclohexane, 52.5 g (874 mmoles) of acetic acid solvent, and 0.951 g (3.82 mmole) of cobalt(II) acetate tetrahydrate, as well as 0.1 g of acetaldehyde as an initiator to avoid an induction period. The reactor was sealed and pressurized to a pressure of 14 atmospheres with a mixture of 50% $O_2$ and 50% $N_2$. The reaction was then carried out at 95° C. for 6 hours. The system was repressurized with oxygen two times when the system pressure indicated consumption of 70–80% of the oxygen. After the reaction was stopped by cooling, the reaction mixture was worked up as described above to recover adipic acid and to prepare the bottoms (which contained catalyst) for recycling. The accumulating bottoms and catalyst were recycled three times for a total of four runs with the following results. By a combination of actual recovery and analysis it was found that the average rate of adipic acid production for the four runs was 3.7 wt %/hr based on the amount of the reaction mixture. The average conversion of cyclohexane was 54.5%. The selectivity to adipic acid was 78.2 mole %, to glutaric acid was 11.1 mole %, and to succinic acid was 5.9 mole %. About 46% of the total adipic acid was recovered by direct filtration of the cooled oxidation effluent. Based on equivalent processing of recycling all of the upper phase and 75% of the lower phase, the amount of bottoms at oxidation equilibrium was 27.2 wt % based on cyclohexane. The adipic acid that could be recycled was about 40.5% of the adipic acid made or about 30.0 wt % based on cyclohexane. Over the course of the four runs, the rate of adipic acid formation dropped by about 34%.

EXAMPLE 3

To the 500-ml 316 stainless steel reactor was added 22.5 g (267 mmoles) of cyclohexane, 52.5 g (874 mmoles) of acetic acid solvent, and 0.951 g (3.82 mmole) of cobalt(II) acetate tetrahydrate, as well as 0.1 g of acetaldehyde as an initiator to avoid an induction period. The reactor was sealed and pressurized to a pressure of 14 atmospheres with a mixture of 50% $O_2$ and 50% $N_2$. The reaction was then carried out at 95° C. for 3.5 hours. The system was repressurized with oxygen two times when the system pressure indicated consumption of 70–80% of the oxygen. After the reaction was stopped by cooling, the reaction mixture was worked up as described above to recover adipic acid and to prepare the bottoms (which contained catalyst) for recycling. The accumulating bottoms and catalyst were recycled three times for a total of four runs with the following results. By a combination of actual recovery and analysis it was found that the average rate of adipic acid production for the four runs was 4.2 wt %/hr based on the amount of the reaction mixture. The average conversion of cyclohexane was 34.5%. The selectivity to adipic acid was 82.3 mole %. About 21% of the total adipic acid was recovered by direct filtration of the cooled oxidation effluent. Based on equivalent processing of recycling all of the upper phase and 75% of the lower phase, the amount of bottoms at oxidation equilibrium was 22.3 wt % based on cyclohexane. The adipic acid that could be recycled was about 59.3% of the adipic acid made or about 29.3 wt % based on cyclohexane. Over the course of the four runs, the rate of adipic acid formation dropped by about 33%.

EXAMPLE 4

To the 500-ml 316 stainless steel reactor was added 15.0 g (178 mmoles) of cyclohexane, 60.0 g (999 mmoles) of acetic acid solvent, and 0.951 g (3.82 mmole) of cobalt(II) acetate tetrahydrate, as well as 0.] g of acetaldehyde as an initiator to avoid an induction period. The reactor was sealed and pressurized to a pressure of 14 atmospheres with a mixture of 50% $O_2$ and 50% $N_2$. The reaction was then carried out at 95° C. for 3.5 hours. The system was repressurized with oxygen two times when the system pressure indicated consumption of 70–80% of the oxygen. After the reaction was stopped by cooling, the reaction mixture was worked up as described above to recover adipic acid and to prepare the bottoms (which contained catalyst) for recycling. The accumulating bottoms and catalyst were recycled three times for a total of four runs with the following results. By a combination of actual recovery and analysis it was found that the average rate of adipic acid production for the four runs was 3.0 wt %/hr based on the amount of the reaction mixture. The average conversion of cyclohexane was 36.9%. The selectivity to adipic acid was 83.1 mole %, to glutaric acid was 9.1 mole %, and to succinic acid was 4.6 mole %. Essentially none of the total adipic acid was recovered by direct filtration of the cooled oxidation effluent. Based on equivalent processing of recycling all of the upper phase and 75% of the lower phase, the amount of bottoms at oxidation equilibrium was 43.9 wt % based on cyclohexane. The adipic acid that could be recycled was about 75.0% of the adipic acid made or about 40.0 wt % based on cyclohexane. Over the course of the four runs, the rate of adipic acid formation dropped by about 43%.

Examples 2 to 4, when compared with Example 1, show that a substantially lower cyclohexane concentration in the oxidation step, although giving much lower reaction rates approximating those of the better published methods), generally leads to higher selectivity and better direct recovery of adipic acid. The low cyclohexane concentration used in Example 4, however, is not conducive to precipitation of adipic acid. The lower conversion conditions used in Examples 3 and 4 provide greater selectivity than the higher conversion conditions of Example 2 but with a reduced direct recovery of adipic acid.

EXAMPLE 5

To the 500-ml 316 stainless steel reactor was added 51.0 g (606 mmoles) of cyclohexane, 24.0 g (400 mmoles) of acetic acid solvent, and 0.238 g (0.955 mmole) of cobalt(II) acetate tetrahydrate, as well as 0.1 g of acetaldehyde as an initiator to avoid an induction period. The reactor was sealed and pressurized to a pressure of 14 atmospheres with a mixture of 50% $O_2$ and 50% $N_2$. The reaction was then carried out at 115° C. for 0.75 hours. The system was repressurized with oxygen two times when the system pressure indicated consumption of 70–80% of the oxygen. After the reaction was stopped by cooling, the reaction mixture was worked up as described above to recover adipic acid and to prepare the bottoms (which contained catalyst) for recycling. The accumulating bottoms and catalyst were recycled three times for a total of four runs with the following results. By a combination of actual recovery and analysis it was found that the average rate of adipic acid production for the four runs was 29.1 wt %/hr based on the amount of the reaction mixture. The average conversion of cyclohexane was 22%. The selectivity to adipic acid was 84.0 mole %. About 80% of the total adipic acid was recovered by direct filtration of the cooled oxidation effluent. Based on equivalent processing of recycling all of the upper phase and 75% of the lower phase, the amount of bottoms at oxidation equilibrium was 6.2 wt % based on cyclohexane. The adipic acid that could be recycled was about 15.0% of the adipic acid made or about 4.8 wt % based on cyclohexane. Over the course of the four runs, the rate of adipic acid formation dropped by about 26%.

EXAMPLE 6

To the 500-ml 316 stainless steel reactor was added 56.25 g (668 mmoles) of cyclohexane, 18.75 g (312 mmoles) of acetic acid solvent, and 0.476 g (1.91 mmole) of cobalt(II) acetate tetrahydrate, as well as 0.1 g of acetaldehyde as an initiator to avoid an induction period. The reactor was sealed and pressurized to a pressure of 14 atmospheres with a mixture of 50% $O_2$ and 50% $N_2$. The reaction was then carried out at 105° C for 1.25 hours. The system was repressurized with oxygen two times when the system pressure indicated consumption of 70–80% of the oxygen. After the reaction was stopped by cooling, the reaction mixture was worked up as described above to recover adipic acid and to prepare the bottoms (which contained catalyst) for recycling. The accumulating bottoms and catalyst were recycled three times for a total of four runs with the following results. By a combination of actual recovery and analysis it was found that the average rate of adipic acid production for the four runs was 21.1 wt %/hr based on the amount of the reaction mixture. The average conversion of cyclohexane was 23.4%. The selectivity to adipic acid was 86.5 mole %. About 85% of the total adipic acid was recovered by direct filtration of the cooled oxidation effluent. Based on equivalent processing of recycling all of the upper phase and 75% of the lower phase, the amount of bottoms at oxidation equilibrium was 6.4 wt % based on cyclohexane. The adipic acid that could be recycled was about 15.0% of the adipic acid made or about 5.3 wt % based on cyclohexane. Over the course of the four runs, the rate of adipic acid formation dropped by about 26%.

EXAMPLE 7

To the 500-ml 316 stainless steel reactor was added 45.0 g (535 mmoles) of cyclohexane, 30.0 g (500 mmoles) of acetic acid solvent, and 0.048 g (0.191 mmole) of cobalt(II) acetate tetrahydrate, as well as 0.1 g of acetaldehyde as an initiator to avoid an induction period. The reactor was sealed and pressurized to a pressure of 14 atmospheres with a mixture of 50% $O_2$ and 50% $N_2$. The reaction was then carried out at 110° C. for 4 hours. The system was repressurized with oxygen two times when the system pressure indicated consumption of 70–80% of the oxygen. After the reaction was stopped by cooling, the reaction mixture was worked up as described above to recover adipic acid and to prepare the bottoms (which contained catalyst) for recycling. The accumulating bottoms and catalyst were recycled three times for a total of four runs with the following results. By a combination of actual recovery and analysis it was found that the average rate of adipic acid production for the four runs was 4.5 wt %/hr based on the amount of the reaction mixture. The average conversion of cyclohexane was 23.5%. The selectivity to adipic acid was 74.2 mole %. About 61% of the total adipic acid was recovered by direct filtration of the cooled oxidation effluent. Based on equivalent processing of recycling all of the upper phase and 75% of the lower phase, the amount of bottoms at oxidation equilibrium was 29.0 wt % based on cyclohexane. The adipic acid that could be recycled was about 29.3% of the adipic acid made or about 8.8 wt % based on cyclohexane. Over the course of the four runs, the rate of adipic acid formation dropped by about 38%.

Examples 5 and 6 provide improved adipic acid recovery and excellent selectivity and show the advantages of high cyclohexane concentration and higher temperatures on rate even when using lower catalyst concentrations. Example 7 shows that good results can be obtained even when using very low catalyst concentrations.

What is claimed is:

1. A process for the oxidative preparation of adipic acid comprising
   (1) reacting
      (a) cyclohexane in the liquid phase and
      (b) an excess, relative to cyclohexane, of oxygen gas or an oxygen-containing gas mixture
   in the presence of
      (c) 0.15 to 15 moles of a solvent per mole of cyclohexane, wherein said solvent comprises an organic acid containing only primary and/or secondary hydrogen atoms and
      (d) at least 0.002 mole per 1000 grams of reaction mixture of a polyvalent heavy metal catalyst,
   wherein the conversion of cyclohexane is no more than about 75%;
   (2) removing the adipic acid by
      (i) cooling the reaction mixture to induce precipitation of the adipic acid and separation of the liquid portion of the reaction mixture into a polar liquid phase and a non-polar liquid phase, and
      (ii) separating the resultant precipitated adipic acid, polar liquid phase, and non-polar liquid phase from one another; and
   (3) recycling intermediates, post-oxidation components, and derivatives thereof remaining after removal of the adipic acid by
      (i) transferring the non-polar liquid phase into reaction step (1) for reaction with oxygen gas or an oxygen-containing gas mixture in the presence of solvent (c) and catalyst (d) and subsequent isolation of the adipic acid, and
      (ii) transferring 10 to 98% by weight of the polar liquid phase into reaction step (1) for reaction with oxygen gas or an oxygen-containing gas mixture in the presence of solvent (c) and catalyst (d) and subsequent isolation of the adipic acid.

2. A process according to claim 1 wherein the conversion of cyclohexane is about 7 to about 30%.

3. A process according to claim 1 wherein component (1)(a) additionally contains a substantially inert diluent that is not cyclohexane.

4. A process according to claim 1 wherein component (1)(b) is oxygen, air, or a mixture of oxygen and an inert gaseous diluent.

5. A process according to claim 1 wherein the partial pressure of oxygen over the reaction mixture of step (1) is from 0.10 to 100 atmospheres absolute.

6. A process according to claim 1 wherein solvent (1)(c) is acetic acid.

7. A process according to claim 1 wherein 0.25 to 1.5 moles of solvent are used per mole of cyclohexane.

8. A process according to claim 1 wherein catalyst (1)(d) is a cobalt salt of an organic acid.

9. A process according to claim 1 wherein catalyst (1)(d) is cobalt(11) acetate.

10. A process according to claim 1 wherein 0.005 to 0.6 mole of catalyst per 1000 grams of reaction mixture are used.

11. A process according to claim 1 wherein reaction step (1) is carried out at a temperature of from 60° to 175° C.

12. A process according to claim 1 wherein in step (2)(ii) the polar liquid phase and non-polar liquid phase are phase separated before the precipitated adipic acid is removed by filtration or centrifugation.

13. A process according to claim 1 wherein in step (2)(ii) the precipitated adipic acid is removed by filtration or centrifugation before the polar liquid phase and non-polar liquid phase are phase separated.

14. A process according to claim 1 wherein the non-polar liquid phase from step (3)(i) is concentrated before being recycled into reaction step (1).

15. A process according to claim 1 wherein further quantities of cyclohexane are added when the non-polar liquid phase from step (3)(i) is recycled into reaction step (1).

16. A process according to claim 1 wherein 50 to 95% by weight of the polar liquid phase from step (3)(ii) is recycled into reaction step (1).

17. A process according to claim 1 wherein 60 to 90% by weight of the polar liquid phase from step (3)(ii) is recycled into reaction step (1).

18. A process according to claim 1 wherein water produced during reaction step (1) is removed from the polar phase of step (3)(ii) by distillation before said polar phase is recycled into reaction step (1).

19. A process according to claim 1 wherein the polar liquid phase from step (3)(ii) is hydrolyzed and additional adipic acid is isolated before said polar liquid phase is recycled into reaction step (1).

20. A process according to claim 1 wherein further quantities of cyclohexane are added when the polar liquid phase from step (3)(ii) is recycled into reaction step (1).

21. A process according to claim 1 wherein both of steps (3)(i) and (3)(ii) are carried out batchwise.

22. A process according to claim 1 wherein either or both of steps (3)(i) and (3)(ii) are carried out continuously.

* * * * *